United States Patent [19]

Doyle

[11] Patent Number: 4,988,195

[45] Date of Patent: Jan. 29, 1991

[54] INTERNAL REFLECTANCE APPARATUS AND METHOD USING CYLINDRICAL ELEMENTS

[75] Inventor: Walter M. Doyle, Laguna Beach, Calif.

[73] Assignee: Axiom Analytical, Inc., Laguna Beach, Calif.

[21] Appl. No.: 312,130

[22] Filed: Feb. 17, 1989

[51] Int. Cl.$^5$ .............................................. G01N 21/01
[52] U.S. Cl. ..................................... 356/244; 356/300
[58] Field of Search ....................... 356/300, 244, 440; 250/339

[56] References Cited

U.S. PATENT DOCUMENTS 3,370,502  2/1968  Wilks, Jr. ......................... 356/246 X
4,595,833  6/1986  Sting ............................... 356/300 X Primary Examiner—Vincent P. McGraw
Attorney, Agent, or Firm—Thomas J. Plante

[57] ABSTRACT

An apparatus and method for fluid sample analysis are disclosed which use a cylindrical internal reflectance element (IRE) having conical end surfaces. The divergence of rays inside the IRE is minimized by using reflecting cones at each end of the IRE, the structural elements and their dimensions being such that each entering ray strikes the conical IRE end surface at substantially the same angle of incidence. Means are included for providing optical stops at the large end of both the input and output reflecting cones, in order to eliminate any rays which might travel through the IRE without first being reflected by the input cone. Using such stops and properly dimensning the entering diameter of the reflecting cone, result in a system in which each ray entering the IRE has been reflected once, and only once, by the reflecting cone.

24 Claims, 10 Drawing Sheets

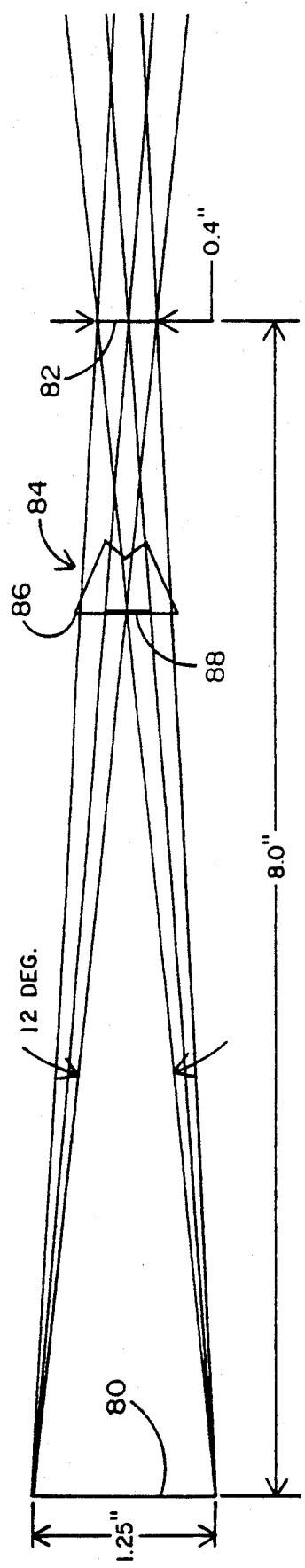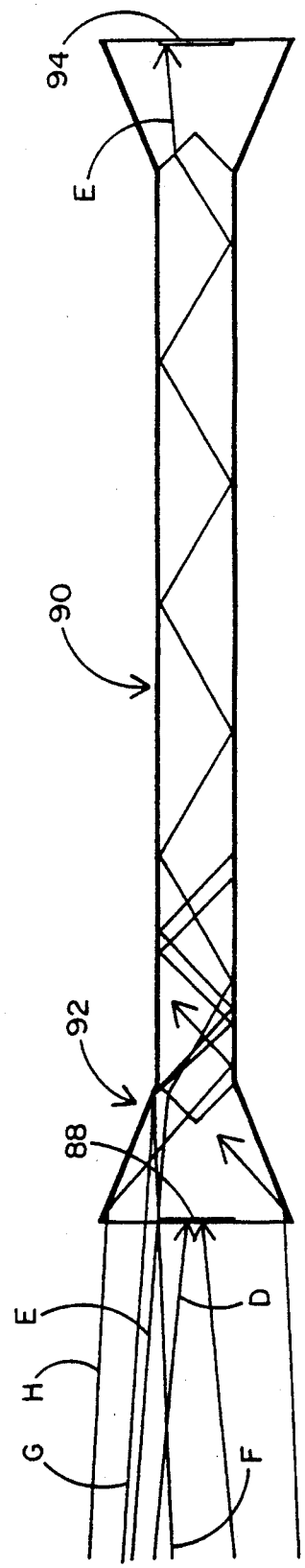
FIG. 11
FIG. 12

INTERNAL REFLECTANCE APPARATUS AND METHOD USING CYLINDRICAL ELEMENTS

BACKGROUND OF THE INVENTION

This invention relates to internal reflectance spectroscopy in which the IREs (internal reflectance elements) are cylindrical. The term "attenuated total reflection" (ATR) is often used in referring to internal reflection spectroscopy.

Although IREs having square cross-sections are widely used, circular cross-section IREs are becoming increasing popular, largely due to their (a) compatibility with reliable and convenient "O" ring seals, (b) advantageous fluid dynamic properties, and (c) compatibility with the circular cross-section IR beam of the typical FTIR spectrometer.

However, there has been considerable concern regarding the extent to which cylindrical IREs can be relied on for quantitative analysis. This concern was addressed by a detailed study carried out by Braue and Pannella on a commercially available IRE, in which mixtures of acetone and water were analyzed in five sets of three runs each carried out over a four month period. The experimenters' report is published in Volume 41, No. 6 (1987) of "Applied Spectroscopy" (pages 1057–1066). Although these authors concluded that precise quantitative analysis of aqueous solutions is possible with cylindrical IREs, they did observe some limitations, including (a) marked dependence of measurement results on positioning of the internal reflectance element, and (b) severe nonlinearity of peak height measurements at high absorbance values.

Although internal reflectance elements (both cylindrical and square cross-section types) are popular, several factors can lead to nonlinearity in their use for internal reflectance spectral measurements. Not least of these is the fact that the internal reflectance process itself becomes highly nonlinear at very high absorbance values, see Harrick "Internal Reflectance Spectroscopy" (1987), pages 22–23 Other sources of nonlinearity include chemical interactions and limited instrument resolution, and finally the dependence of measured absorbance on the angle of incidence of the IR radiation. This last factor is the primary subject of the present disclosure.

The internal reflection phenomena are inherently highly dependent on angle of incidence of the radiation at the interface between the internal reflectance element and the analyte. As can be seen from the computer-generated curves in Harrick's book (supra), a 10° change in incidence angle can easily lead to a factor-of-two change in effective sample thickness and hence in measured absorbance. If radiation covering a range of angles is used, the results will be analogous to those obtained when a wedged cell is used in transmission spectroscopy. As has been discussed in detail by Hirschfeld in "Fourier Transform Infrared Spectroscopy", Vol 2 (Ed Ferraro & Basile 1979), pages 193–239, this situation gives rise to a nonlinear dependence of measured absorbance on the concentration of the chemical being measured. In the case of the wedged cell, the data can, in principle, be corrected if the wedge thickness and angle are known. This is not the case in internal reflectance spectroscopy, since the dependence of effective thickness on the angle is nonlinear, and the angular distribution will generally not be well characterized. Thus, to obtain linear data using IREs, it is necessary to minimize the angular spread of rays traveling through the internal reflectance element.

The present invention is addressed to the deficiencies in the prior art devices. An early and structurally simple use of cylindrical IREs is shown in Wilks U.S. Pat No. 3,370,502, which discloses an IRE "cylinder or rod" having conical ends for entering and exiting radiation. In FIG. 3 of Wilks, "a cone 30 whose inner walls 31 are reflective is used to direct the incoming rays to the end 32 substantially perpendicular to the end surface thereof This arrangement is particularly suited for incoming parallel rays such as in spectrophotometers. The exit end 33 has a similar cone 34 for directing the rays to an indicating or recording portion of the spectrophotometer" (Col. 2, lines 50–56).

The Wilks design has major deficiencies, resulting from the wide range of angles at which different rays in the entering and exiting collimated beams strike the end surfaces and internal surfaces of the IRE.

Sting U.S. Pat. No. 4,595,833 relates to "reflaxicon optics" "for directing infrared radiation into the entry end of the cylindrically shaped internal reflection element, as well as for collecting radiation from the exit end of the element" (Col. 5, lines 11–14). Sting criticizes the device of the Wilks U.S. Pat. No. (3,370,502) in column 4, lines 4–10: "This configuration is indicated to be particularly suited for incoming parallel rays (collimated source infrared radiation), such as in spectrophotometers. However, the funnel-shaped mirror optics undesirably have a wide variation in angle of incidence. Furthermore, difficulties arise in focusing the emergent infrared radiation onto the detector".

The rather complex device used by Sting in an effort to solve the problem of "wide variation in angle of incidence", which device is referred to in sales literature as the "Circle-Cell®", itself has a significant angle divergence problem. This is the device which Braue and Pannella (supra) used in their tests.

IRE (ATR) sampling systems may be designed for use either with collimated or with focused radiation. In the case of the Circle Cell®, the focused beam in the spectrometer's sample compartment is intercepted and sharply focused onto the conical end of an IRE crystal. Within the crystal, rays can have incidence angles, at the interface with the analyte, ranging from typically 40° to 49°. With this wide range of angles, the effective sample thickness can vary as much as a factor of two. In addition, the rays which are more strongly absorbed at each reflection also experience the greatest number of reflections These two interrelated effects combine to give rise to a very strong dependence of absorption on incidence angle. Given the wide range of angles (40° to 49°) employed in the Circle Cell®, these dual effects serve to seriously degrade linearity of the analytical data.

SUMMARY OF THE INVENTION

The present invention minimizes the divergence of rays entering and exiting the conical ends of a cylindrical IRE by using reflecting cones at each end of the IRE, the structural elements and their dimensions being such that each entering ray strikes the conical IRE end surface at substantially the same angle of incidence. Means are included for providing optical stops at the large end of at least one, and preferably both, of the input and output reflecting cones, in order to eliminate any rays which might travel through the IRE without first being reflected by the input cone. Using such stops and properly dimensioning the entering diameter of the reflecting cone, result in structure in which each ray entering the IRE has been reflected once, and only once, by the reflecting cone.

In the present invention, virtually all of the rays traveling through the IRE lie within a narrow range of angles, and strike the crystal/analyte interface the same umber of times. The result is a very high degree of absorbance linearity (adherence to Beer's law) even for strongly absorbing bands.

Although the angular divergence of rays in the present invention is least when a collimated input beam is used, the present invention also provides a significant improvement over prior art devices when the input beam is a focused beam.

In one version of the present invention, a Cassegrain objective is used at each end of the IRE, the smaller mirrors, one in each Cassegrain, providing the desired optical stops for eliminating rays not reflected by the reflecting cone.

BRIEF DESCRIPTION OF THE DRAWINGS

FIGS. 11 and 12 show schematically the advantages of the present invention, if the input radiation (infrared) is a focused beam, instead of the collimated beam shown in FIGS. 3-9.

DETAILED DESCRIPTION OF THE SPECIFIC EMBODIMENTS

Figure 1:
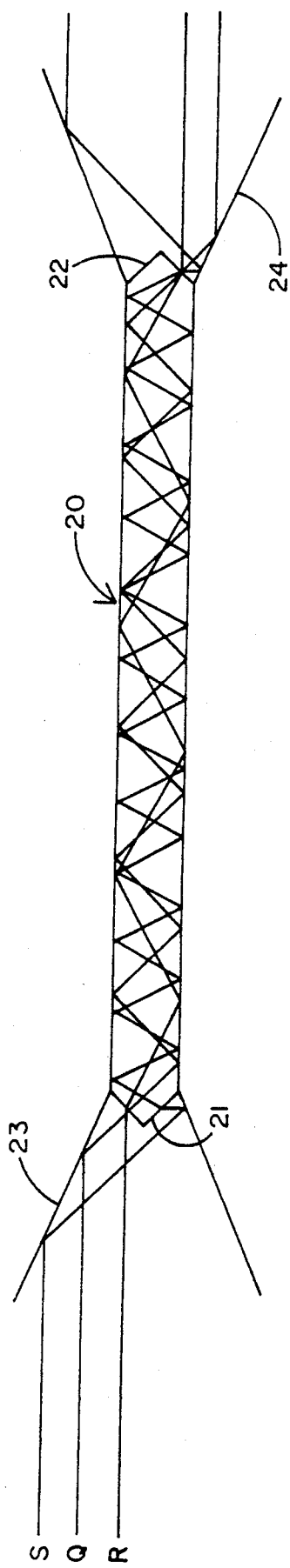
FIG. 1 traces the paths of rays in a radiation beam traversing a device of the type shown in FIG. 3 of Wilks U.S. Pat. No. 3,370,502.
Figure 2:
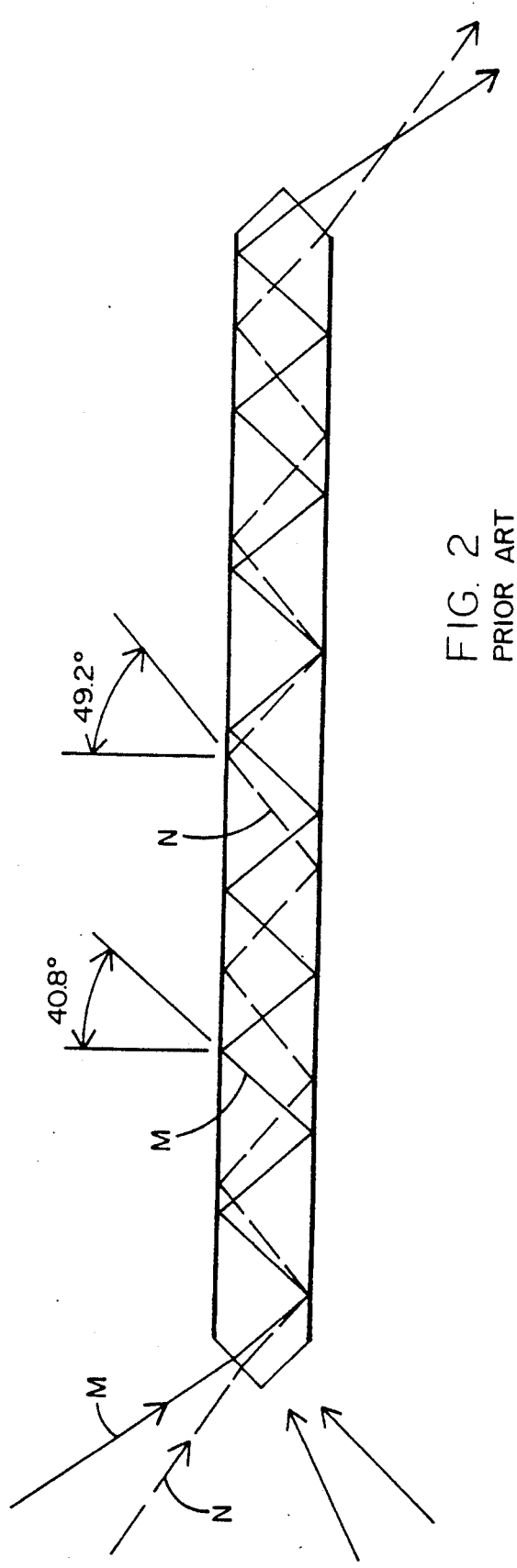
FIG. 2 traces the paths of rays in a radiation beam traversing a device of the type shown in FIG. 2 of Sting U.S. Pat. No. 4,595,833.

FIGS. 1 and 2 show why the prior art efforts to provide ideal performance in cylindrical IREs are deficient.

FIG. 1 shows an IRE structure similar to that of Wilks U.S. Pat. No. 3,370,502 (FIG. 3) The Wilks patent disclosed a very simple design, in which radiation was coupled into and out of the conical ends of a circular cross-section IRE rod by means of reflecting cones at each end Sting U.S. Pat. No. 4,595,833 dismisses this design approach by stating that "funnel-shaped mirror optics undesirably have a wide variation in angle of incidence". To understand the origin of this statement, refer to FIG. 1.

FIG. 1 shows a circular cross-section IRE 20, whose ends 21 and 22 are conical, each cone having a 90° included angle. Light is coupled into and out of these conical ends by means of reflecting cones 23 and 24, whose sides make a 22.5° angle with the axis of the IRE. If collimated input radiation is assumed, three different coupling conditions can occur, as illustrated by the three rays shown. Ray Q strikes the IRE 20 at normal (perpendicular) incidence after a single reflection from the reflecting cone. It is then repetitively reflected at the interface between the IRE and the sample at an angle of 45°. This angle is roughly optimum for many typical samples—yielding a fairly large absorption depth.

Ray R strikes the end 21 of the IRE without first striking the reflecting cone 23. Since its angle of incidence at the input surface of the IRE is 45°, it is refracted on entering the IRE rod. It strikes the interface between the IRE and the sample at an incidence angle of approximately 62°. At this angle, the effective absorption depth is substantially less than at 45°.

Ray S strikes the reflecting cone 23 twice and then strikes the end 21 of the IRE at an incidence angle of 45° on the opposite side of the normal (perpendicular) from ray R It is refracted and strikes the IRE/sample interface at an incidence angle of approximately 28°.

A device having the characteristics of FIG. 1 would be analogous to a parallel combination of three transmission cells having different thicknesses. Data taken with such a device would be highly nonlinear, making quantitative analysis quite difficult. The angular range of 28° to 62° (34°) in IRE/analyte incidence would result in the unsatisfactory performance correctly diagnosed by Sting U.S. Pat. No. 4,595,833. As stated above, the internal refelction phenomenon is inherently highly dependent on angle of incidence of the radiation at the interface between the IRE and the analyte.

Although the Circle Cell ® optics of Sting U.S. Pat. No. 4,595,833 reduce substantially the divergence of the IRE/analyte angles of incidence of rays in the IRE, their divergence is still approximately 8.5° (49.2°-40.8°), a divergence too great to obtain linear measurements. Another problem with the Circle Cell ® optics is, as stated by Braue and Pannella, supra, that "repositioning of the Circle Cell ® optical bench between runs and the micro-boat sampling cell between samples critically affects the quantification results".

FIG. 2 illustrates the angle of incidence deviation in a Circle Cell ® IRE device. As shown in U.S. Pat. No. 4,595,833, a fairly sophisticated optical device, called a "reflaxicon", is used to focus radiation directly into the conical entrance surface of the IRE, and to collect radiation emerging from the exit surface. The "reflaxicon" has the property of providing a focus when viewed in any axial plane (i e., a plane containing the IRE axis), while retaining circular symmetry about this axis.

While the Circle Cell ® does not exhibit the problem of multiple distinct incidence angles exhibited by the device of FIG. 1, it is characterized by a range of incidence angles In fact this range can be quite wide. The geometry illustrated in FIG. 2 of the Sting patent is typical of the commercial Circle Cells ®. As discussed, starting at column 9, line 53, of the patent, it provides a 2.5×magnification of the IRE surface. When used with a spectrometer having f:7.5 focused beam sample-region optics, it results in a net f:#equal to f:3 at the IRE. This corresponds to a total included angle of approximately 19°.

In a focal plane of a typical optical system, each point is illuminated by radiation from all areas of the focusing optics. Thus, it can be assumed that, for the above Circle Cell ® example, each illuminated point on the surface of the IRE will receive radiation with a full range of incidence angles up to 9.5° from the normal, with inclinations in all possible directions A high percentage of these will be significantly skewed (i.e., will make a large angle with the nearest axial plane). This situation can lead to a significant diversity of paths followed by the various rays within the IRE. This problem has been pointed out in "Data Sheet #10", published by Harrick Scientific Corporation.

The Circle Cell ® structure used by Braue and Pannella, supra, employed focused radiation striking the IRE element at angles ranging from 35° to 55° from the axis. With the ZnSe element used, this spread would result in incidence angles ranging from about 41° to 49° at the interface between the analyte and the IRE, as illustrated in FIG. 2 (note the paths of rays M and N). This range is sufficient to give rise to more than a 50% variation of effective sample thicknesses. In addition, as can be seen from the figure, those rays which have the lower incidence angles, and which are therefore more strongly absorbed at each reflection, also experience a greater number of reflections. For the conditions shown, the range is from 10 to 14 reflections. These two interrelated effects combine to give rise to a strong dependence of absorbance on incidence angle. This effect can easily account for the reported nonlinear behavior.

FIG. 2 further illustrates the fact that, with the wide range of angles employed, there is little correlation between the angle of propagation of a ray and its position on exiting the rod. As a result, any movement of the internal reflectance element relative to the focal point of the output collecting optics can lead to selective and unpredictable vignetting of the angular distribution of rays. This effect is enhanced if the end of the rod is not overfilled by the image of the detector. The result is a random change in the average effective sample thickness, and hence in the absorbance linearity and calibration of the system.

Another serious concern is the sensitivity of the Circle Cell's performance to the positioning of the IRE relative to the input "reflaxicon" optics. The reflaxicon provides input radiation in the form of a sharply converging annular cone. It is essential that the entrance cone of the IRE be precisely centered at the apex of the radiation cone. Any shift in the position of the IRE will lead to a significant change in the distribution of ray positions and angles seen by the IRE, and hence in the distribution of optical paths within it. The fact that this can lead to gross changes in data has been pointed out by Braue and Pannella (supra).

Figure 3:
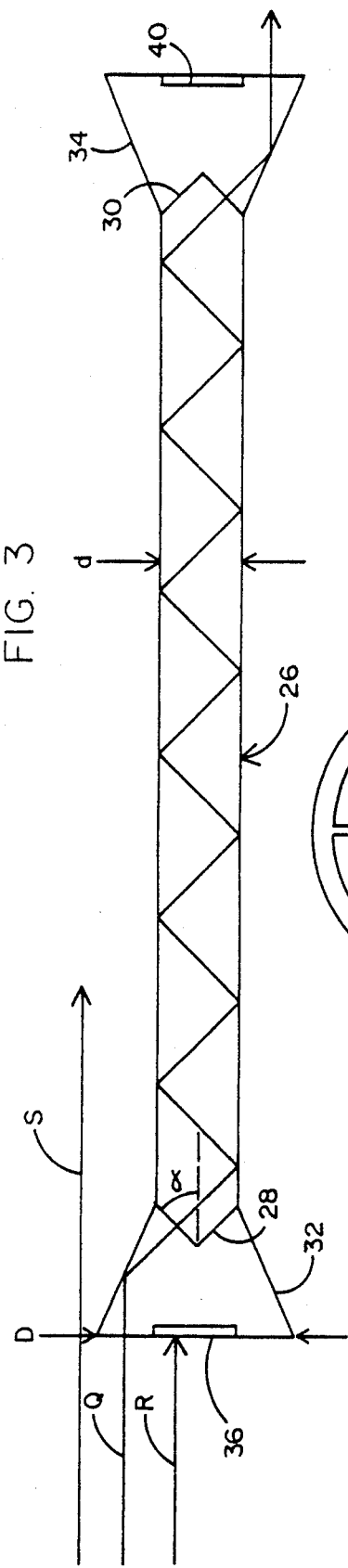
FIG. 3 is a schematic showing the basic concepts of the present invention, including ray tracings of certain incoming rays.

The present invention, one embodiment of which is shown in FIG. 3, illustrates a simple structure for solving the prior art problems FIG. 3 includes a ray pattern for rays which represent the spatial range of those passing through the IRE, based on the assumption of an essentially collimated entering beam.

A cylindrical IRE 26 is shown, which has a convex conical entering end 28, and a convex conical exiting end 30. A concave conical reflector 32 is positioned adjacent the IRE entering end 28, and a concave conical reflector 34 is positioned adjacent the IRE exiting end 30 This structure is similar in appearance to FIG. 3 in Wilks U.S. Pat. No. 3,370,502. However, the problems which Wilks failed to recognize have been diagnosed and cured in the present invention.

In order to prevent the presence of rays in the IRE which degrade its performance, it is necessary to limit the rays in the IRE to those having substantially the same characteristics as ray Q in FIG. 1. That ray is reflected once by the conical reflector 32 in FIG. 3, and enters the conical end 28 of the IRE on a path perpendicular to the conical end surface.

Figure 4:
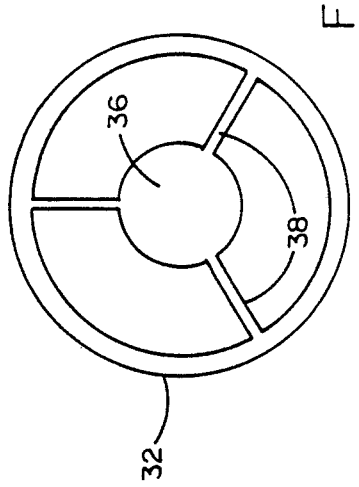
FIG. 4 is an end view of a structure which supports a ray blocking stop at the entrance of the IRE in FIG. 3.

The present invention is so constructed that outer rays, such as ray S, which in FIG. 1 are reflected by the conical reflector twice, in FIG. 3 miss the conical reflector entirely. Furthermore, inner rays, such as ray R, which in FIG. 1 are not reflected by the conical reflector, are blocked from entering the IRE 26 by a stop 36 located at or near the large diameter end of conical reflector 32. The stop 36 may be supported by spider arms 38, as seen in FIG. 4, looking toward the entering end of conical reflector 32.

Preventing the outer rays from entering the IRE depends on correct determination of the maximum diameter of conical reflectors 32 and 34. For a practical IRE fabricated from ZnSe, the IRE cone half angle (alpha) will be typically 45°; and the conical reflector half angle (beta) will be half of that, or 22.5°. In that situation, the relation of the IRE diameter "d" and the maximum allowable diameter "D" of the conical reflector will be: D=2.414d.

Derivation of that value of D is based on the following equation, which also applies to other assumptions concerning the values of alpha and beta:

$$D = d\left(1 + \cos 2\text{ beta} + \frac{\sin 2\text{ beta}}{\tan\text{ alpha}}\right).$$

The structure illustrated in FIGS. 3 and 4, as stated above, employs a stop 36 to block rays which would otherwise enter the IRE 36 directly without first striking the conical reflector 32. The optimum diameter for this stop 36 is probably approximately equal to the diameter of the IRE 26.

Figure 5:
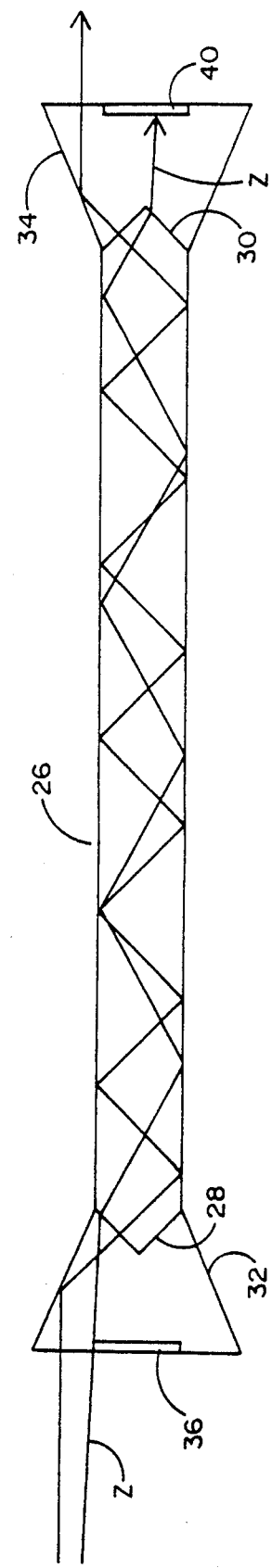
FIG. 5 adds to FIG. 3 a ray tracing which shows the blocking effect of a stop located at the exit of the IRE.

Even with nominally collimated radiation, a typical ray will make a finite angle with the axis of the system. Thus, some rays which pass the entry stop 36 will be inclined sufficiently toward the axis to enter the IRE directly. However, the length of the IRE can be chosen so that such rays, which necessarily must enter near the outer edge of the IRE, will exit at a point distant from the outer cone edge, where it will be intercepted by a second stop 40 at the large end of the second conical reflector 34, which reflector recollimates the beam. This situation is illustrated in FIG. 5, in which ray Z, which enters the conical end of IRE 26 without being reflected by conical reflector 32, is blocked by stop 40 after exiting from conical end 30 of the IRE. The optimum length of the IRE can be determined for a given situation by ray analysis in sketches, or with computer assistance.

Figure 6:
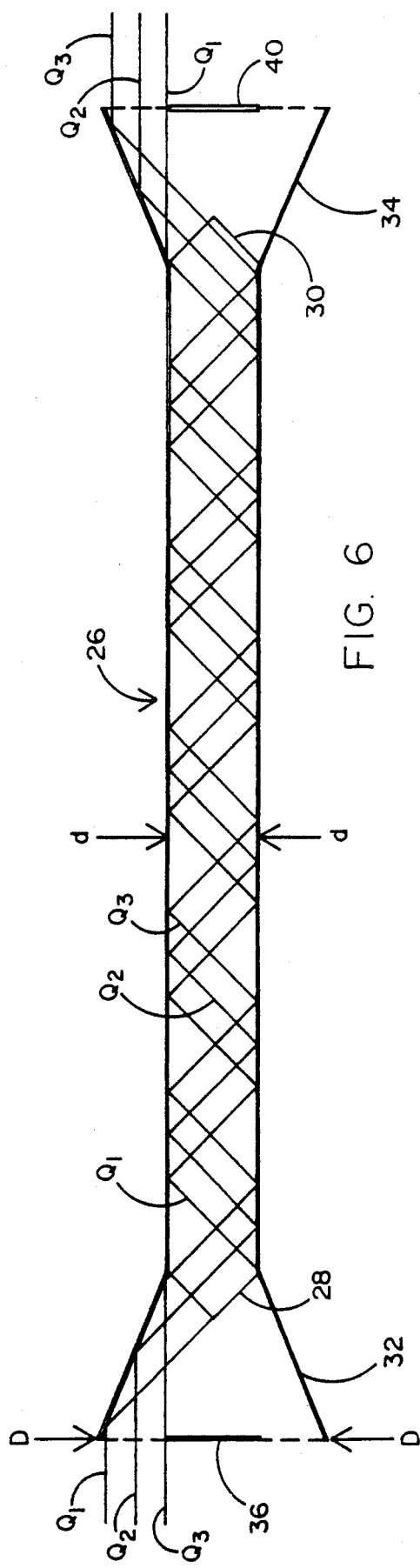
FIG. 6 is a more detailed showing of the invention, included tracing of several rays which follow the desired paths in the IRE.

FIG. 6 shows essentially the same structure as FIGS. 3-5. However, in FIG. 6 a plurality of parallel rays $Q_1$, $Q_2$ and $Q_3$ are traced through the IRE 26, each ray entering and exiting on a path perpendicular to the conical ends of the IRE, and each impinging on the sample-contacting periphery of the IRE at 45° angles.

In the foregoing description of FIGS. 3-6, it has been assumed that the desired angle of incidence at the IRE/sample interface is 45°. This is a highly desirable angle of incidence for an IRE, or cell, fabricated from zinc selenide However, IRE materials other than zinc selenide, e.g., germanium, would have different optimum angles of incidence in the IRE. The optimum angle of IRE/sample incidence for germanium would be approximately 30°. The nature of the sample to be analyzed also affects the optimum angle of IRE/sample incidence; but sample variation is a relatively minor factor in angle of incidence selection.

The desired angle of IRE/sample incidence essentially determines the values of other angles in the structure. In other words, the included angle of the conical IRE end, and the angle between the conical reflector and the central axis, or axis of symmetry, of the radiation beam (and IRE), may need to be changed to accommodate different IRE materials.

The use of zinc selenide results in simple angle values If a 45° angle of incidence of the IRE/sample is desired, the included angle of the IRE conical entering end should be 90°; and the angle between the entering conical reflecting mirror and the axis of the structure should be 22.5°. The same angles should be used for the conical exiting end of the IRE and for the exiting conical reflecting mirror.

If a different angle of IRE/sample interface is desired, both the included angle of the IRE conical end and the angle of the conical reflecting mirror should be changed. Also the ratio of the diameter of the large end of the entering conical mirror to the diameter of the IRE should be changed.

In the case of zinc selenide, the perpendicularity of rays entering the conical IRE end provides the maximum collecting aperture, thus enhancing radiation throughput. In other situations, the maximum collecting aperture may be obtained by using a direction of entering rays other than perpendicular.

Figure 7:
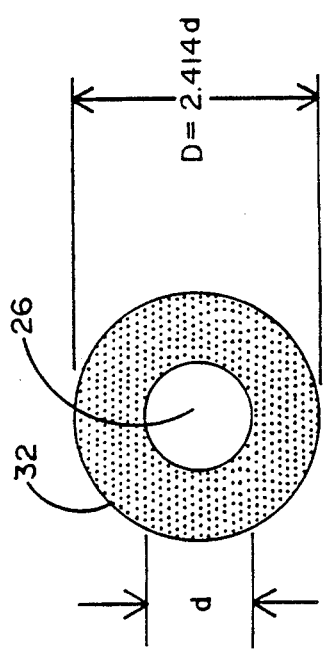
FIG. 7 is an end view which shows the ratio of two significant diameters in the structure which limits radiation entering the IRE.

In FIG. 7, the ratio of the maximum reflector cone diameter to the IRE diameter is shown, with dots simulating the rays which enter the IRE through the available annular area, The diameter of IRE 26 in FIG. 7 may be substantially equal to the size of stop 36, as stated above However, this dimensional relationship may be varied.

In many situations, it will be desirable to restrict the diameter of the IRE, so as to maximize the number of reflections which interact with the sample. For example, if the 6 mm diameter rod typically used in a Circle Cell ® were employed, the maximum diameter of the input cone would be 14.5 mm. This is about half of the beam diameter obtained from many FTIR spectrometers In such situations, it is desirable to use a beam condenser/expander structure to match the FTIR beam to the sampling device Although several different designs are feasible, the use of Cassegrain optics is particularly attractive, both because the coaxial nature of the Cassegrain minimizes overall size, and because the central obscuration inherent in the Cassegrain design can serve as the stop required to eliminate the undesired central rays.

Figure 8:
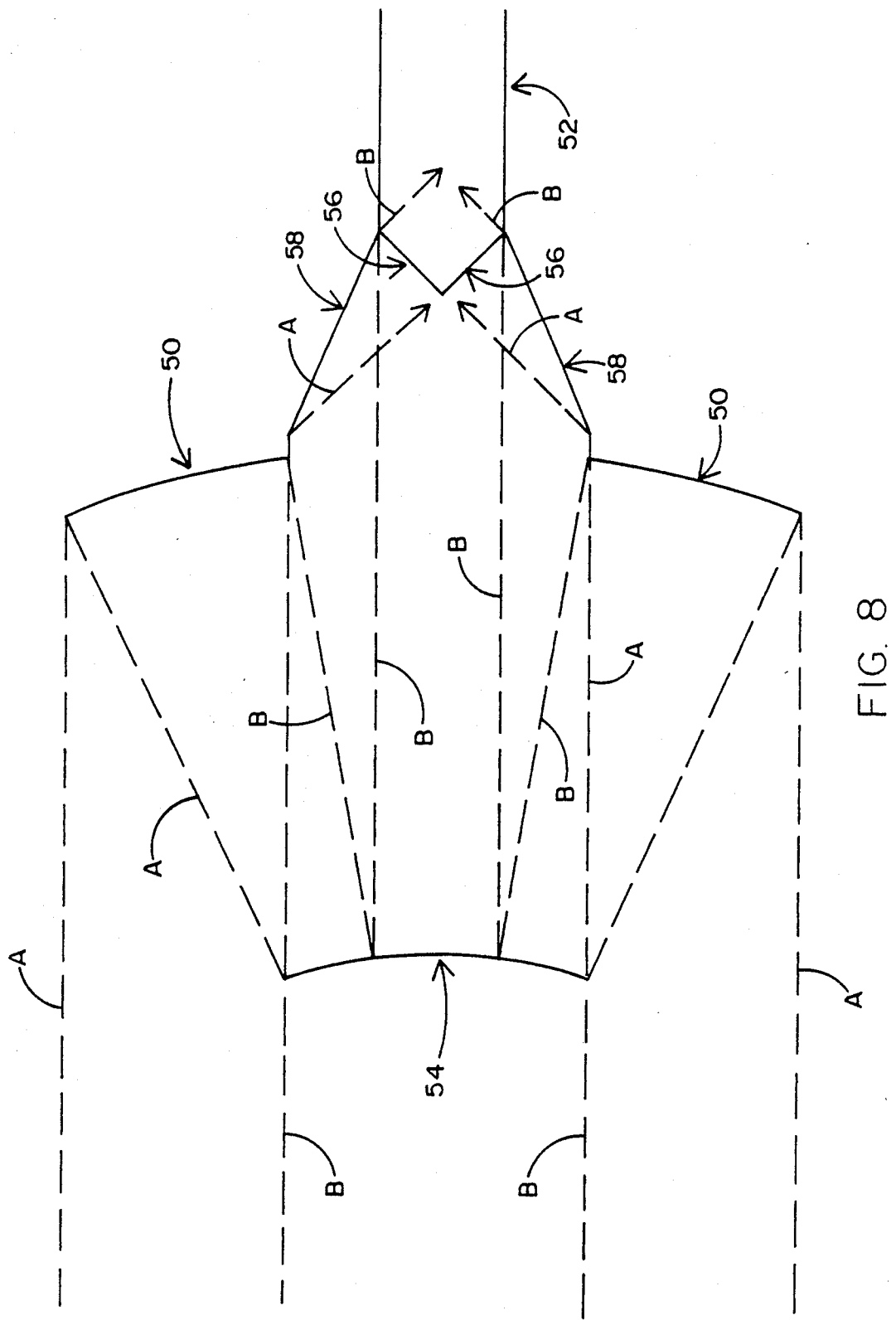
FIGS. 8 and 9 illustrate the use of Cassegrain objectives at the input and output ends of the structures shown in FIGS. 3-7.

This configuration is shown in FIG. 8. A Cassegrain is used, which is adjusted to receive and emit collimated beams, after reducing the beam diameter and increasing its intensity. The dashed lines represent the extreme rays (parallel to the axis) that are transmitted by the Cassegrain. The design parameters are set so that the outer rays match the maximum allowed outer reflecting cone diameter, and the inner rays are aligned with the outer edge of the IRE. In this case, the obscuration due to the smaller (secondary) mirror of the Cassegrain maps onto the end of the IRE, and thus provides the needed stop.

As shown in FIG. 8, the Cassegrain comprises: (a) a larger concave annular mirror 50 having a central aperture larger than, but aligned with, a cylindrical IRE 52; and (b) a smaller convex mirror 54 which receives incoming radiation reflected by larger mirror 50, and reflects such radiation into end 56 of the IRE. Although Cassegrains are usually associated with converging or diverging beams, in FIG. 8 Cassegrain 50/54 inputs and outputs collimated beams. The applicant has discovered that, contrary to "conventional wisdom" (Sting U.S. Pat. No. 4,595,833, column 3, lines 51-61), using a Cassegrain beam condenser/expander in conjunction with nominally collimated radiation actually provides a highly advantageous arrangement, which results in minimum angular divergence of the rays incident on the IRE/analyte interface.

In FIG. 8, the outer rays A in the approaching beam are first reflected from the outer edge of annular mirror 50 to the outer edge of mirror 54, and are then reflected to the large diameter edge of reflecting cone 58. After reflection from cone 58, rays A move into IRE 52 along paths which are perpendicular to its cone-shaped end 56, and which enter near its apex. The inner rays B in the approaching beam are first reflected from the inner edge of annular mirror 50 to mirror 54, and are then reflected to the small diameter edge of reflecting cone 58. After reflection from cone 58, rays B move into IRE 52 along paths which are perpendicular to its cone-shaped end 56, and which enter near its periphery.

Figure 9:
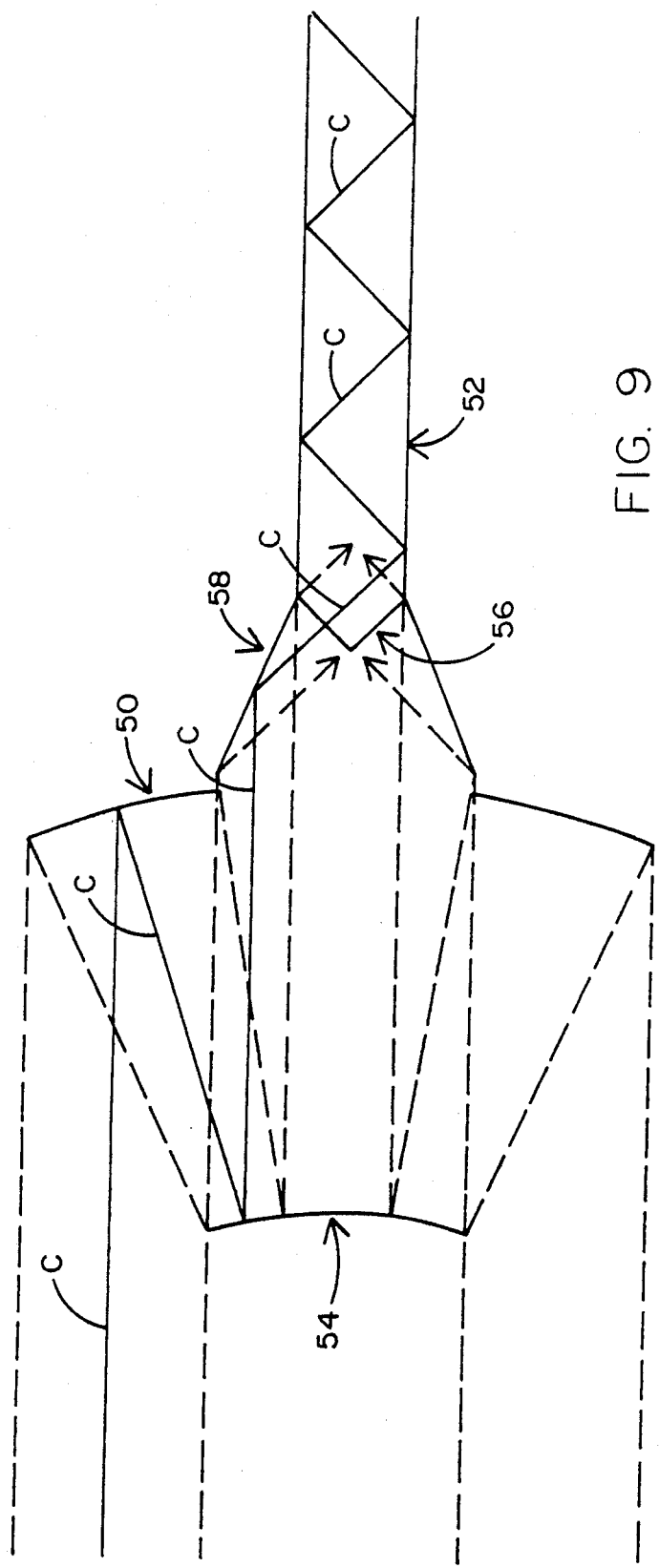

FIG. 9, in addition to tracing outer and inner rays A and B of FIG. 8, includes a center ray C which is reflected first by mirror 50, then by mirror 54, then by reflecting cone 58, along a path perpendicular to the conical end surface of IRE 52. As it passes through the IRE, ray C has an angle of incidence of 45° with the outer cylindrical wall of the IRE.

The present invention, as illustrated in FIGS. 3-9, in which essentially collimated beams are used entering and exiting the structure, is able to limit the divergence of virtually all rays in the IRE to less than ±1°. In other words, the angle of incidence of rays at the IRE/sample interface can be maintained within 1° of the selected value of 45°. And all rays will experience the same number of reflections at the IRE/sample interface The result is a very high degree of absorbance linearity (adherence to Beer's Law), even for strongly absorbing bands. In a set of recently conducted experiments, the structure of the present invention, used in a deep immersion environment, obtained linearity within 3% for concentrations ranging from 0.05% to 50% acetone (in water).

Another significant advantage of the structure of the present invention is the fact that the relationship between the IRE position and the various optical elements is fixed by the mechanical design. In fact, the conical reflectors which direct the radiation into the IRE are supported by the same structure as the IRE itself. No misalignment can take place because optical alignment is designed into the mechanical structure As a result, a given device will provide the same results run after run, making true infrared quantitative analysis of liquids a reality.

Furthermore, if desired, movement along the axis can be allowed so as to allow compensation for variations in IRE length Even if such relative axial movement is allowed, there will be minimal effect on system performance, since all of the rays entering the ends of the IRE are near normal incidence at the conical input surface. Axial misadjustment will simply reduce the number of rays which can pass through the IRE, but will not materially change the distribution of incidence angles or path lengths.

Figure 10:
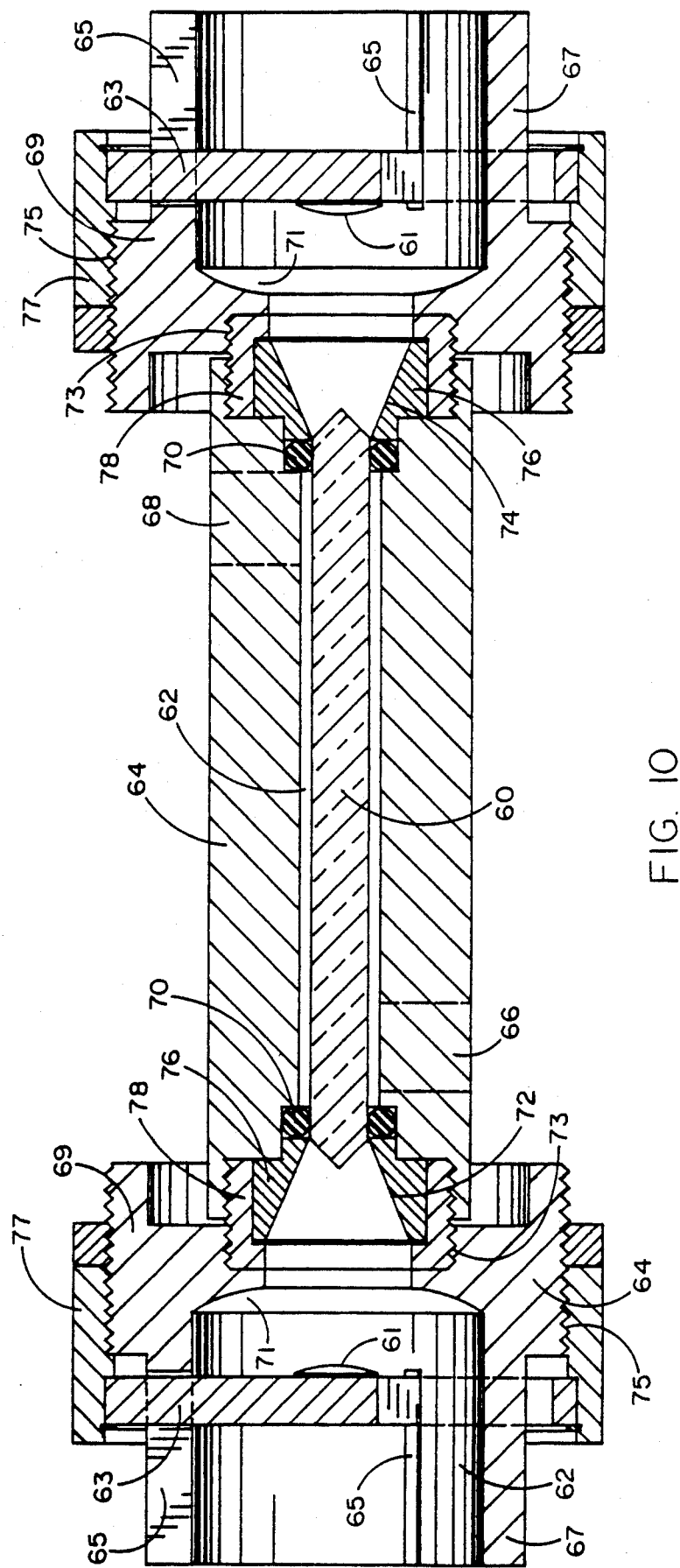
FIG. 10 shows, partly in cross-section, a relatively detailed and complete hardware embodiment of the concepts illustrated in FIGS. 3-9.

A practical structure employing the principles of the present invention is shown in FIG. 10. An IRE 60 is mounted inside an annular, longitudinally extending sample chamber 62, which is located inside a solid metal body 64. Inlet and outlet ports 66 and 68 permit sample fluid to flow through the annular chamber 62. An O ring 70 is used to seal each end of chamber 62.

Each end of IRE 60 is supported by one of the O-rings 70, which also engages the inner lip of one of two conical reflectors 72 and 74. The conical reflectors are each formed as an inner surface of an annular metal element 76. Each metal element 76 is retained in position in body 64 by a nut 78 having a threaded periphery engaging a threaded opening at one end of body 64.

Cassegrain supporting structures are secured to each end of body 64. The two structures, which may be identical, each include a small centered convex mirror 61, which is held in place by three spider arms 63, one of which is shown in cross-section. In each Cassegrain supporting structure, the spider arms slide into slots 65, formed in an extending cylindrical portion 69 of a metal Cassegrain housing 69. An inner wall of each housing 69 has secured thereto an element which provides an annular concave mirror surface 71 facing toward the small centered mirror 61. Each Cassegrain body 69 has a threaded inner periphery 73 in engagement with threaded outer periphery of nut 78, and the threaded outer periphery 75 in engagement with a threaded inner periphery of an outer assembly-securing nut 77.

In FIGS. 3-10, the optical structures at the radiation entering and exiting ends are symmetrical. This is generally desirable, but not entirely necessary. The angles used at the IRE entering and exiting ends and at both conical reflectors should be the same at both ends. The maximum diameter of the exiting conical reflector could be larger than that of the entering conical reflector, since the problem of peripheral rays from the source does not exist at the exit of the IRE. The use of a Cassegrain at the exiting end is not as important as the use of a Cassegrain at the entering end. However, structures of the type disclosed herein are often inserted into systems in which the diameters of the beam coming from the source and the beam leading to the detector are identical; so the beam reduction and beam expansion need to be matched. Another option available in using the present invention is the use of a single-ended IRE, in which both the entering radiation and the exiting radiation pass through the same end of the IRE, and its other end is flat.

Although, as stated above, the minimum angular ray divergence at the IRE/analyte interface is obtained with a collimated entering beam, the apparatus of the present invention also provides better performance than prior art structures when a nominally focusing beam is the entering beam.

FIG. 11 illustrates a typical focused beam configuration. In this case, a nominally collimated IR beam (diameter 1.25") is focused by a focusing optical element, such as a parabolic reflector (here indicated schematically by the straight vertical line 80 at the left of the figure). After it passes through the center of the sample compartment, the beam is recollimated by a second optical element (not shown).

As long as the spectroscopic resolution is not too great, the usable area in the center of the sample region will generally correspond to the image of the infrared detector. Assuming a combination of a 1 mm detector, 0.8" focal length detector optics, and 8.0" focal length sample region optics, this combination yields a foucused beam diameter at 82 of 1 cm (approximated in FIG. 11 by 0.4").

The rays shown in the figure correspond to the extreme rays, i.e., the rays which emanate from the outer edges of the focusing optics and pass through both outer edges of the beam focus. Two rays through the center of the focus are also shown. The maximum angle between any two rays in this example is 12 degrees, as indicated.

Superimposed on top of the ray paths is an outline of the input end 84 of the ATR cell of the present invention. As can be seen, all of the rays in this example fall within the area defined by the outer circumference 86 of the collecting cone. The more sharply converging rays are blocked by the central stop 88. Thus the angular spread of rays striking either side of the collecting aperture will be considerably less than 12 degrees.

FIG. 12 is a more detailed view of the paths of the extreme rays which fall within the open aperture of the collecting optics. For illustration, one extreme ray (ray D) is included, which strikes the input stop 88. Ray E is a ray which misses the input stop, but is angled downwardly, so that it strikes the end of the IRE rod 90 without first striking the reflecting cone 92. The path of this ray has been traced all the way through the IRE, in order to show that it will eventually strike the second stop 94. Thus, while some percentage of rays can enter the IRE 90 without first being reflected from the cone 92, only a small percentage of these will also miss the second stop 94. As noted above, the length of the IRE 90 can be chosen to minimize the possibility of undesired rays missing both the input and output stops 88 and 94.

In FIG. 12, ray F is the extreme ray which emanates from the lowest possible point on the input optics, consistent with its missing the input stop 88 and striking the reflecting cone 92. Ray G is the lowest ray emanating from the upper edge of the focusing optics which is able to strike the reflecting cone 92. Finally, ray H is the extreme upper ray.

Rays F and G clearly correspond to the extreme angular limits of rays which can pass through the ATR (IRE) cell 90. For the cases shown, the spread between them is 6 degrees. After these rays enter the ZnSe IRE (refractive index=2.4), the angular spread will be reduced, and all of the rays striking the IRE/analyte interface will lie within a range of about 2.5 degrees. Since the system is axially symmetric, rays which enter the lower portion of the input cone will also strike the interface within this same range of angles.

As the above discussion has shown, in the focused beam case, the use of a central stop has a second benefit, beyond preventing rays from entering the rod without first striking the reflecting cone 92. It also selectively discriminates against rays which make large angles with the system axis, thus restricting the angular spread within the IRE rod.

The Circle Cell ® (supra) does not have a central obstruction. In fact, depending on the exact placement in the focused beam, almost the full range of ray angles can strike one side of the first element of the reflaxicon optics. This range would be 12 degrees for the FIG. 2 example. By focusing the beam onto the end of the rod, the reflaxicon further increases the total divergence angle. Commercial units have been reported to illuminate each side of the rod with typically a 20 degree distribution of angles. This translates into roughly 8 degrees within the IRE.

Although the central stop of the present invention does discard some optical energy, it has been found experimentally that the transmission of the IRE in applicant's configuration is at least 20%. This is comparable with that obtained with the Circle Cell ®.

Figure 13:
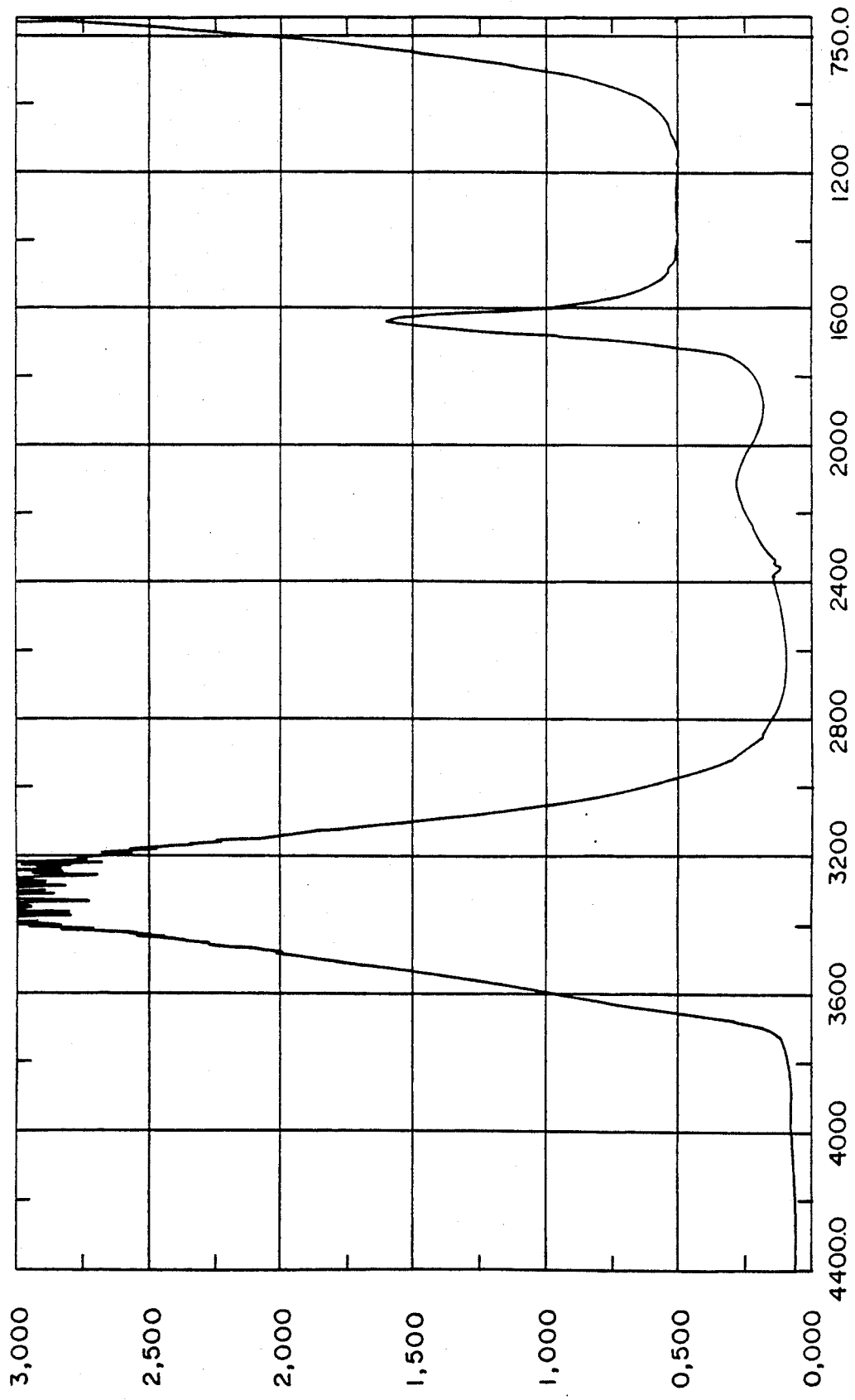
FIGS. 13 and 14 show spectral data obtained using the present invention with two different liquid samples.
Figure 14:
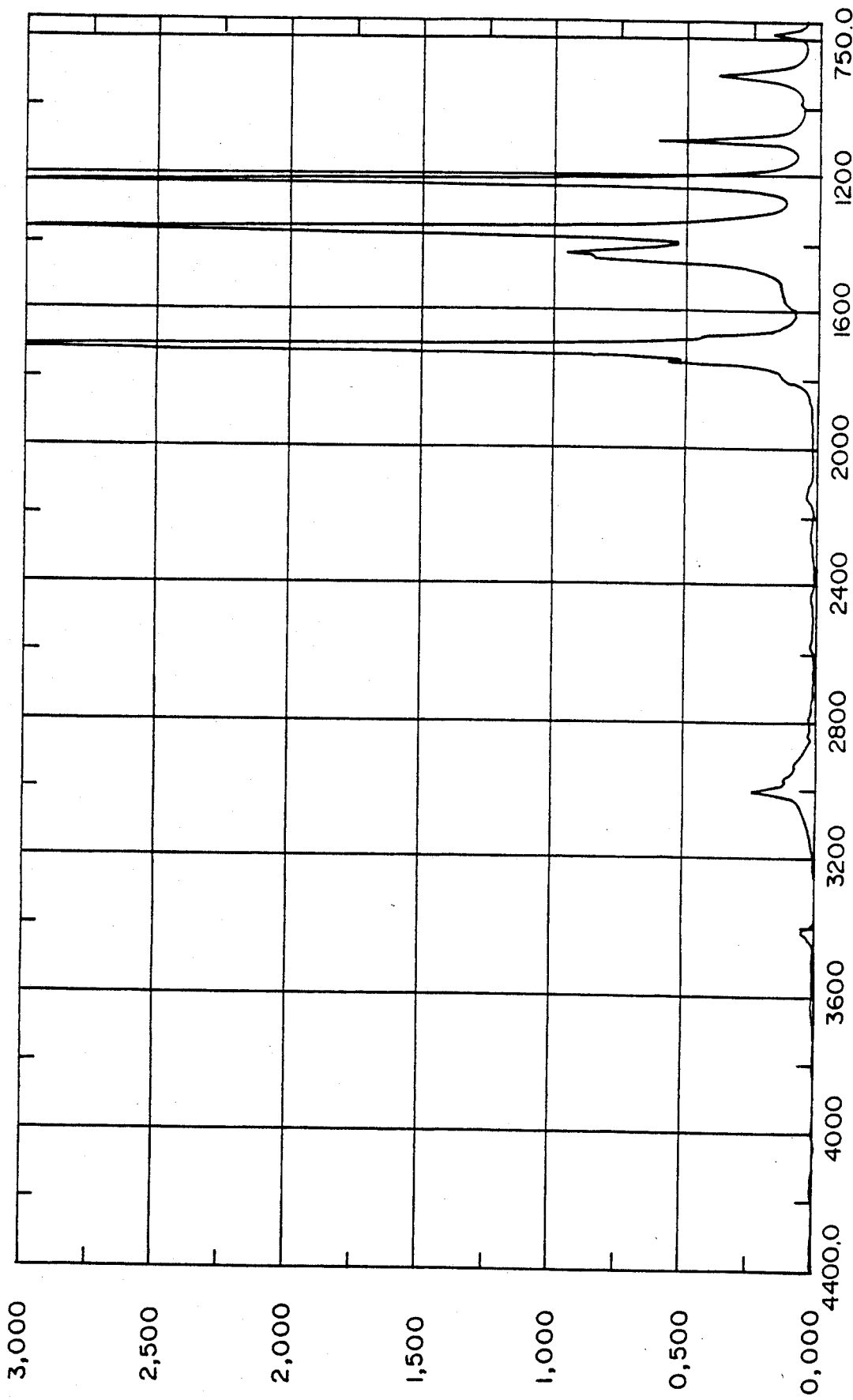

FIGS. 13 and 14 are spectra obtained using the structure of the present invention in its basic form illustrated in FIGS. 3–7, i.e., without the Cassegrains. For these measurements, the device was mounted in the focused beam of a conventional FTIR spectrometer sample compartment. The optical configuration thus corresponded to that illustrated in FIG. 12. The IRE dimensions and mechanical structure were such as to provide approximately 11 reflections at the IRE/analyte boundary.

FIGS. 13 and 14 correspond to absorbance spectra of pure water and pure acetone, respectively. In both cases, the absorbance values obtained for the various peaks are typically between two and three times greater than those obtained for the same substances using other cylindrical internal reflectance devices (refs: Braue and Pannella, Sprouse Collection).

The enhanced absorption illustrated in FIGS. 13 and 14 is an expected result of the herein disclosed apparatus. By restricting the incidence angles, the present structure maximizes the total absorption, and eliminates the nonlinear effects which result from summing the contributions from a range of incidence angles.

To provide a direct comparison with the linearity data of Braue and Pannella, supra, an immersible version of the herein disclosed apparatus was tested, utilizing collimated input radiation and an IRE prividing five reflections at the analyte interface. A series of water-/acetone mixtures were prepared, ranging from 0.16% to 50% acetone by volume. After each measurement, the device was dried, and any remaining liquid was wicked out from around its "O" ring seals before it was dipped into the next mixture.

Figure 15:
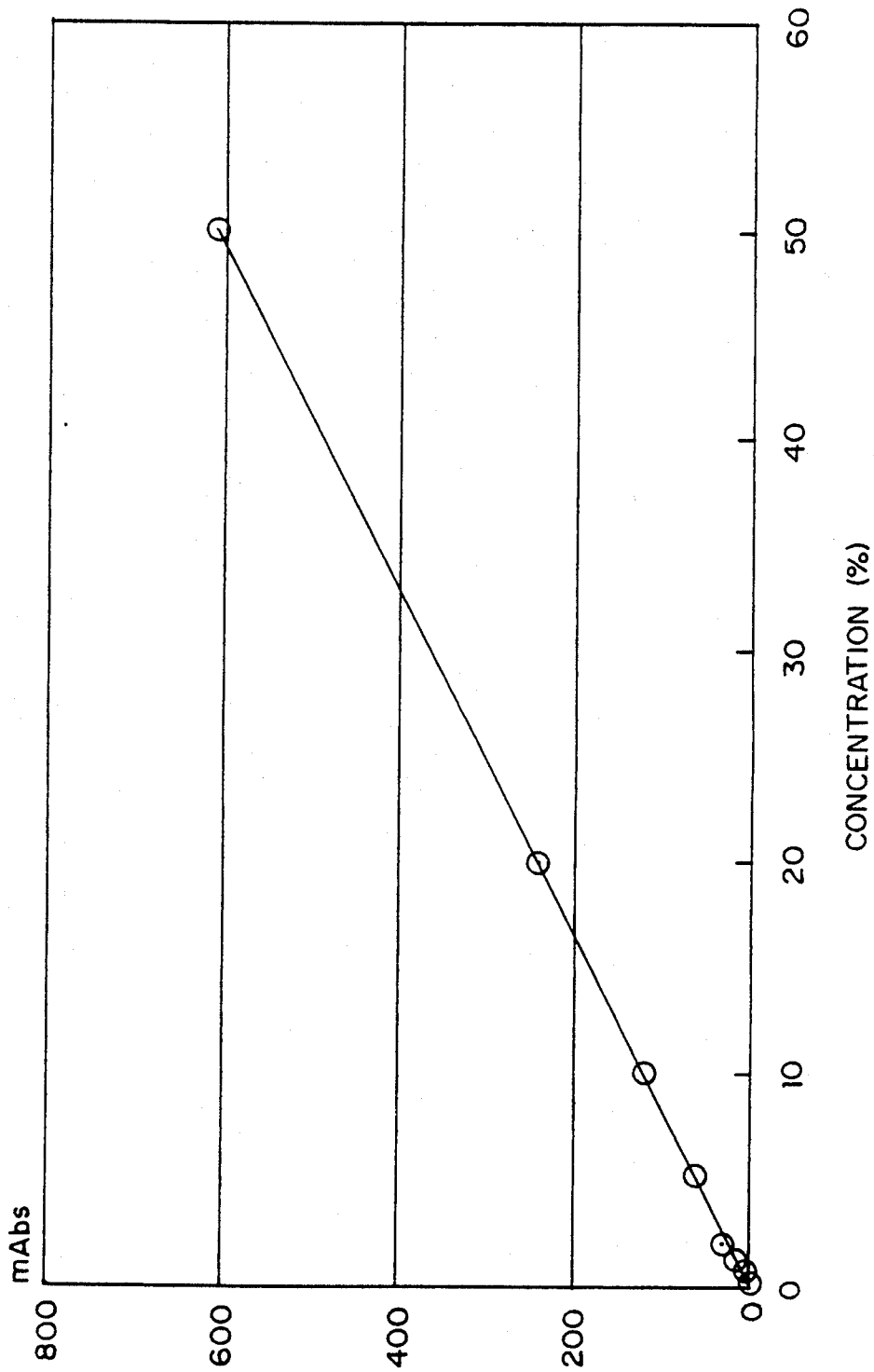
FIG. 15 is a plot of measured peak absorbance versus known concentration for a series of samples measured using the apparatus of the present invention.

FIG. 15 is a plot of the measured peak absorbance versus the known concentration, for all of the samples in the series, with a straight line drawn between the origin and the highest measured absorbance With the exception of two of the low concentration points, all of the data points fell within approximately 3% of the straight line fit. This is in marked contrast to the data obtained by Braue and Pannella. Their experimental results were typically 12% and 28% below the linear fit at 20% and 50% acetone concentration, respectively.

From the foregoing description, it will be apparent that the apparatus and method disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. An optical system, for use in analyzing fluids by means of attenuated total reflection, in which an internally reflecting element extends into a fluid whose radiation absorption is to be measured, comprising:

a small diameter cylindrical cross-section internally reflecting element, inside which radiation travels generally longitudinally as it is reflected back and forth across the diameter of the element;

a convex conical surface on the radiation entering end of the internally reflecting element;

a mirror for reflecting incoming radiation into the entering end of the internally reflecting element;

the mirror having a concave conical reflecting surface, the smaller diameter end of which is adjacent to the entering end of the internally reflecting element;

means for directing a radiation beam into the larger diameter end of the mirror;

the maximum diameter of the mirror being too small to accept incoming rays which would be reflected more than once by the mirror on their way to the entering end of the internally reflecting element; and means near the entering end of the internally reflecting element for blocking rays which would otherwise enter that element without being reflected by the mirror.

2. The optical system of claim 1 in which the beam directed into the conical mirror is a substantially collimated beam.

3. The optical system of claim 1 in which the beam directed into the conical mirror is a substantially focused beam.

4. The optical system of claim 1 which also comprises:

a Cassegrain objective which receives a larger diameter incoming beam and directs a smaller diameter, intensified beam into the conical reflecting mirror and internally reflecting element.

5. The optical system of claim 4 in which the Cassegrain objective comprises:

a larger concave annular mirror which reflects the incoming radiation beam; and a smaller convex round mirror which reflects radiation received from the larger annular mirror into the conical reflecting mirror and internally reflecting element, and which substantially blocks the portion of the incoming radiation beam which otherwise would enter the internally reflecting element without being reflected by the conical reflecting mirror.

6. The optical system of claim 1 which also comprises:

a convex conical surface on the radiation exiting end of the internally reflecting element;

a mirror having a concave conical reflecting surface which reflects the radiation after it exits the internally reflecting element;

the two conical end surfaces of the internally reflecting element having the same included angles; and the two conical mirror surfaces having the same angles with the axis of symmetry of the radiation.

7. The optical system of claim 1 in which:
the convex conical surface on the radiation-entering end of the internally reflecting element has a 90° included angle; and
the concave conical mirror surface makes an angle of 22.5° with the axis of symmetry of the internally reflecting element.

8. The optical system of claim 7 in which:
the radiation rays entering the internally reflecting element are substantially perpendicular to its entering surface; and
the radiation rays travelling inside the internally reflecting element have angles of incidence of approximately 45° with its sides.

9. The optical system of claim 1 in which the ratio of the maximum diameter D of the conical reflecting mirror to the diameter d of the internally reflecting element is calculated using the following expression:

$$D = d\left(1 + \cos 2\beta + \frac{\sin 2\beta}{\tan \alpha}\right).$$

10. The optical system of claim 9 in which the ratio of diameter D to diameter d is approximately 2.414.

11. The method of analyzing fluids which comprises:
locating a cylindrical internally reflecting element in a fluid sample which is to be analyzed;
directing radiation toward one end of the internally reflecting element by means of a concave conical reflector having a maximum diameter which will not allow more than one impingement of an entering ray on said reflector;
directing radiation from the conical reflector into a convex conical entering end of the internally reflecting element;
blocking rays which otherwise would pass through the internally reflecting element without being reflected by the conical reflector; and
providing angles of the conical reflector and of the conical end surface of the internally reflecting element which (a) cause the rays inside the internally reflecting element to have predetermined substantially identical angles of incidence at the interface of the sample and the periphery of the internally reflecting element, and (b) cause substantially all the rays inside the internally reflecting element to have a predetermined equal number of reflections at said interface.

12. The method of claim 11 in which blocking of rays occurs before they enter the internally reflecting element.

13. The method of claim 12 in which blocking of rays also occurs after they exit the internally reflecting element.

14. An optical system, for use in analyzing fluids by means of attenuated total reflection, in which an internally reflecting element extends into a fluid whose radiation absorption is to be measured, comprising:
a small diameter cylindrical cross-section internally reflecting element, inside which radiation travels generally longitudinally as it is reflected back and forth across the diameter of the element, said internally reflecting element having a convex conical surface on its radiation entering end; and
radiation directing means controlling radiation beams which pass through the internally reflecting element in such a way that substantially all radiation rays in such a beam have substantially identical angles of incidence at the sides of the internally reflecting element, and substantially all of such rays are reflected the same number of times on the sides of the internally reflecting element;
said radiation directing means including a mirror which reflects radiation into the entering end of the internally reflecting element, and which has a concave conical reflecting surface whose smaller end is adjacent to the internally reflecting element.

15. The optical system of claim 14 in which the radiation directing means comprises:
means for causing each radiation beam to enter the larger diameter end of the concave conical mirror;
the diameter of said larger diameter end of the mirror being too small to accept incoming rays which would be reflected more than once by said mirror on their way to the entering end of the internally reflecting element; and
blocking means near at least one end of the internally reflecting element for blocking rays which would otherwise pass through the internally reflecting element without being reflected by the mirror.

16. The optical system of claim 15 in which the beam directed into the conical mirror is a substantially collimated beam.

17. The optical system of claim 15 in which the blocking means is located near the entering end of the internally reflecting element to block rays which would otherwise enter said element.

18. The optical system of claim 15 in which the blocking means is located near the exiting end of the internally reflecting element to block rays which would otherwise be transmitted from said element.

19. The optical system of claim 15 in which the blocking means comprises:
a first blocking element near the entering end of the internally reflecting element to block rays which would otherwise enter said element; and
a second blocking element near the exiting end of the internally reflecting element to block rays which would otherwise be transmitted from said element.

20. The optical system of claim 15 which also comprises:
a Cassegrain objective which receives a larger diameter incoming beam and directs a smaller diameter, intensified beam into the conical reflecting mirror and internally reflecting element.

21. The optical system of claim 20 in which the Cassegrain objective comprises:
a larger concave annular mirror which reflects the incoming radiation beam; and
a smaller convex round mirror which reflects radiation received from the larger annular mirror into the conical reflecting mirror and internally reflecting element, and which substantially blocks the portion of the incoming radiation beam which otherwise would enter the internally reflecting element without being reflected by the conical reflecting mirror.

22. The optical system of claim 14 which also comprises:
a convex conical surface on the radiation exiting end of the internally reflecting element;

a mirror having a concave conical reflecting surface which reflects the radiation after it exits the internally reflecting element;

the two conical end surfaces of the internally reflecting element having the same included angles; and the two conical mirror surfaces having the same angles with the axis of symmetry of the radiation.

23. The optical system of claim 14 in which:

the convex conical surface on the radiation-entering end of the internally reflecting element has approximately a 90° included angle; and the concave conical mirror surface makes an angle of approximately 22.5° with the axis of symmetry of the internally reflecting element.

24. The optical system of claim 23 in which:

the radiation rays entering the internally reflecting element are substantially perpendicular to its entering surface; and the radiation rays travelling inside the internally reflecting element have angles of incidence of approximately 45° with its sides.

* * * * *